United States Patent [19]
Tartre

[11] Patent Number: 5,992,213
[45] Date of Patent: Nov. 30, 1999

[54] METHOD FOR TESTING SOIL CONTAMINATION

[76] Inventor: André Tartre, 540 rue Marin, Longueuil, Canada

[21] Appl. No.: 09/118,888

[22] Filed: Jul. 20, 1998

Related U.S. Application Data

[63] Continuation-in-part of application No. 08/718,505, Oct. 4, 1996, Pat. No. 5,786,527.

[51] Int. Cl.⁶ .............................. G01N 33/24; G01N 1/24
[52] U.S. Cl. .................. 73/19.01; 73/864.74; 73/864.43
[58] Field of Search .................. 73/19.01, 19.12, 73/31.07, 864.41, 864.43, 864.81, 864.74, 864.33; 175/21, 59

[56] References Cited

U.S. PATENT DOCUMENTS

| | | |
|---|---|---|
| 3,180,983 | 4/1965 | Hall et al. . |
| 3,307,912 | 3/1967 | Davis . |
| 3,685,345 | 8/1972 | Wise . |
| 3,714,811 | 2/1973 | Diagle et al. . |
| 3,857,289 | 12/1974 | Wise et al. . |
| 4,335,622 | 6/1982 | Bartz . |
| 4,452,091 | 6/1984 | Richers . |
| 4,804,050 | 2/1989 | Kerfoot . |
| 5,786,527 | 7/1998 | Tartre . |

*Primary Examiner*—Michael Brock
*Attorney, Agent, or Firm*—François Martineau

[57] ABSTRACT

A method for locally testing soil contamination by determining the generation rate of a contaminant fluid in porous soil, including the steps of injecting a purging fluid in the soil through a probe while simultaneously collecting fluid samples in the ground with the probe and measuring therein the contaminant concentrations, until an equilibrium is reached, i.e. until there is no variation of the contaminant fluid concentration. Afterwards, a tracer gas such as oxygen is continuously injected into the soil through the probe at a known flow rate in addition to the purging fluid, and in a small quantity relative to the second fluid, while fluid samples are collected wherein the tracer gas concentrations are measured. With the above-mentioned measured concentrations of the contaminant fluid and the tracer gas, the generation rate by the soil of the contaminant fluid may be computed.

10 Claims, 2 Drawing Sheets

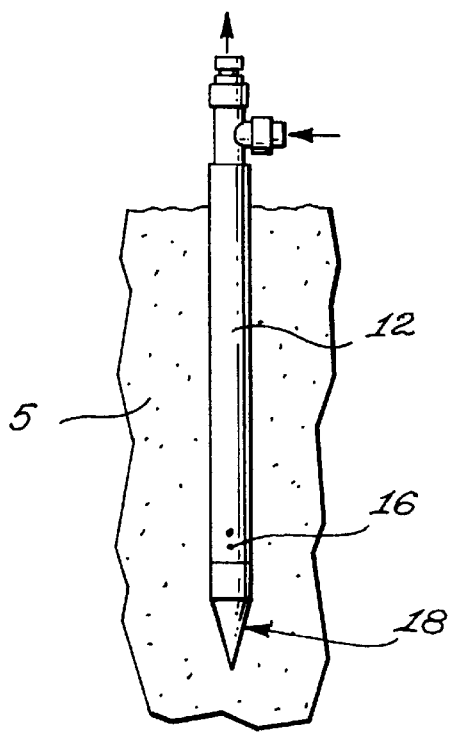
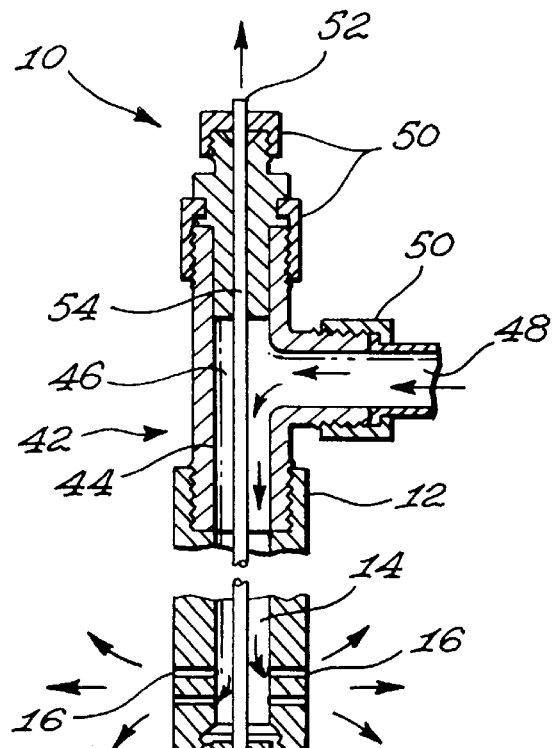
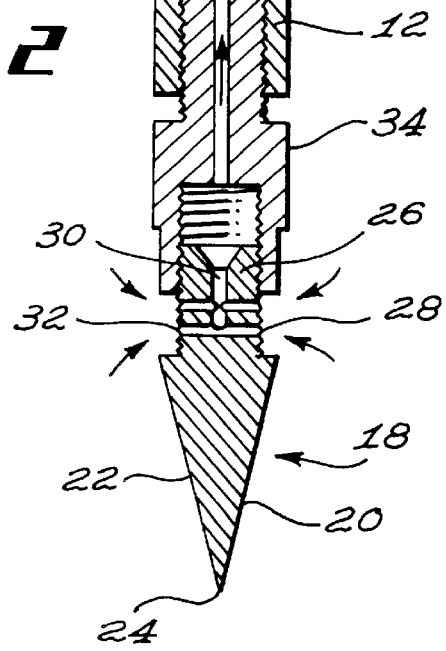
Fig. 1
Fig. 2

METHOD FOR TESTING SOIL CONTAMINATION

This application is a Continuation-In-Part of parent U.S. patent application No. 08/718,505 filed by this applicant on Oct. 4, 1996, and allowed Feb. 11, 1998, U.S. Pat. No. 5,786,527.

FIELD OF THE INVENTION

The present invention relates to soil contamination testing either in laboratory or in situ, and more particularly to a method for testing soil contamination in situ by measuring a volatile or gazeous contaminant generation rate.

BACKGROUND OF THE INVENTION

U.S. Pat. No. 3,685,345 issued in 1972 to H. L. Wise describes a soil-gas sampling device and method therefor. The Wise device requires that a bore be drilled in the ground, and thereafter it be sealingly plugged with a suitable cover, to prevent air infiltration in the bore. An inlet pipe and an outlet sampling pipe extend through the cover into the ground bore, both pipes being connected to a pump. A circulation fluid (or fluid vector) is pumped through the inlet pipe, so that it comes into repetitive contacts with the bottom portion of the surrounding earth formation. The outlet pipe recovers an equal amount of fluid, and concentration data concerning a selected fluid may be acquired from the outlet fluid thus retrieved, by known means.

Wise teaches that the relevant information concerning the soil condition will be obtained when the rate of change of the concentration of the selected fluid repetitively exposed is low relative to its rate of change in the early stages of the fluid circulation. Thus, Wise offers a method for testing soil in which the concentration of the fluid in the earth formation is evaluated by means of a fluid vector.

An important disadvantage of the Wise method is that a bore has to be drilled into the ground for the testing to be accomplished. This step prolongs the whole operation significantly, and the total boring time may become very significant where many fluid concentration readings have to be accomplished in a single site. Moreover, if the site would have to be tested deeper into the soil, then the boring operation would become proportionally longer.

Another important disadvantage of the Wise method is that the results obtained thereby give the concentration of the selected fluid in the soil. This is disadvantageous especially if the Wise method was to be used to evalutate a soil contaminated by an hydrocarbon or a chlorinated solvent. The concentration of a selected fluid in the soil does not necessarily give a direct relationship with the concentration of the contaminant in the area. Fluid contaminants migrate in porous soil, which can lead to erroneous positive contamination results. This migration is influenced by many parameters such as the nature of the soil (its porosity, organic content, moisture content, . . . ) and the nature of the contaminant. Indeed, the relative presence in a sample of the volatile or gazeous contaminant does not necessarily indicate its proximity to the pollution since migration can and does occur. The spreading or extension of the contamination near underground fuel supply tanks, for example, cannot be determined efficiently by the Wise method, which will provide the concentration of the vapor or gazeous contaminant fluid in the soil by means of the circulation of its vector fluid.

OBJECT OF THE INVENTION

It is the gist of the present invention to provide a contamination soil testing method for determining the generation rate by the soil of one or more contaminant fluids, that will improve upon the testing method disclosed in the U.S. Pat. No. 3,685,345 to Wise.

SUMMARY OF THE INVENTION

The present invention relates to a method for locally testing underground soil contamination by determining the generation rate of a first contaminant fluid in porous soil, said method comprising the steps of:

a) continuously injecting a second fluid in the soil at a substantially constant flow rate;

b) simultaneously collecting fluid samples in the soil at least at regular time intervals near the area where said second fluid is injected in the soil;

c) measuring the concentrations of said first fluid in the fluid samples collected in step b);

d) once there is substantially no variation of the concentration of said first fluid in successive fluid samples according to the measurements accomplished in step c), injecting—in addition to said second fluid—a tracer gas at a constant flow rate and in a small quantity, relative to said second fluid;

e) at the latest once step d) is started, measuring the concentrations of said tracer gas in the fluid samples collected in step b); and f) computing from the concentrations measured in steps c) and e) the first fluid generation rate in the soil.

The present invention also relates to a method for locally testing underground soil contamination by determining the generation rate of a first contaminant fluid in porous soil, said method comprising the steps of:

a) continuously injecting a second fluid and a tracer gas in the soil at substantially constant respective flow rates;

b) simultaneously collecting fluid samples in the soil at least at regular time intervals near the area where said second fluid is injected in the soil;

c) measuring the concentrations of said first fluid and of said tracer gas in the fluid samples collected in step b);

d) computing from the concentrations measured in steps c) the first fluid generation rate in the soil.

DESCRIPTION OF THE DRAWINGS

In the annexed drawings:

FIG. 1 is a side elevation showing the device for carrying out the method of the present invention, operationally inserted in soil to be tested;

FIG. 2 is an enlarged side elevation showing the device of FIG. 1; and

DETAILED DESCRIPTION OF THE EMBODIMENTS

Figure 3:
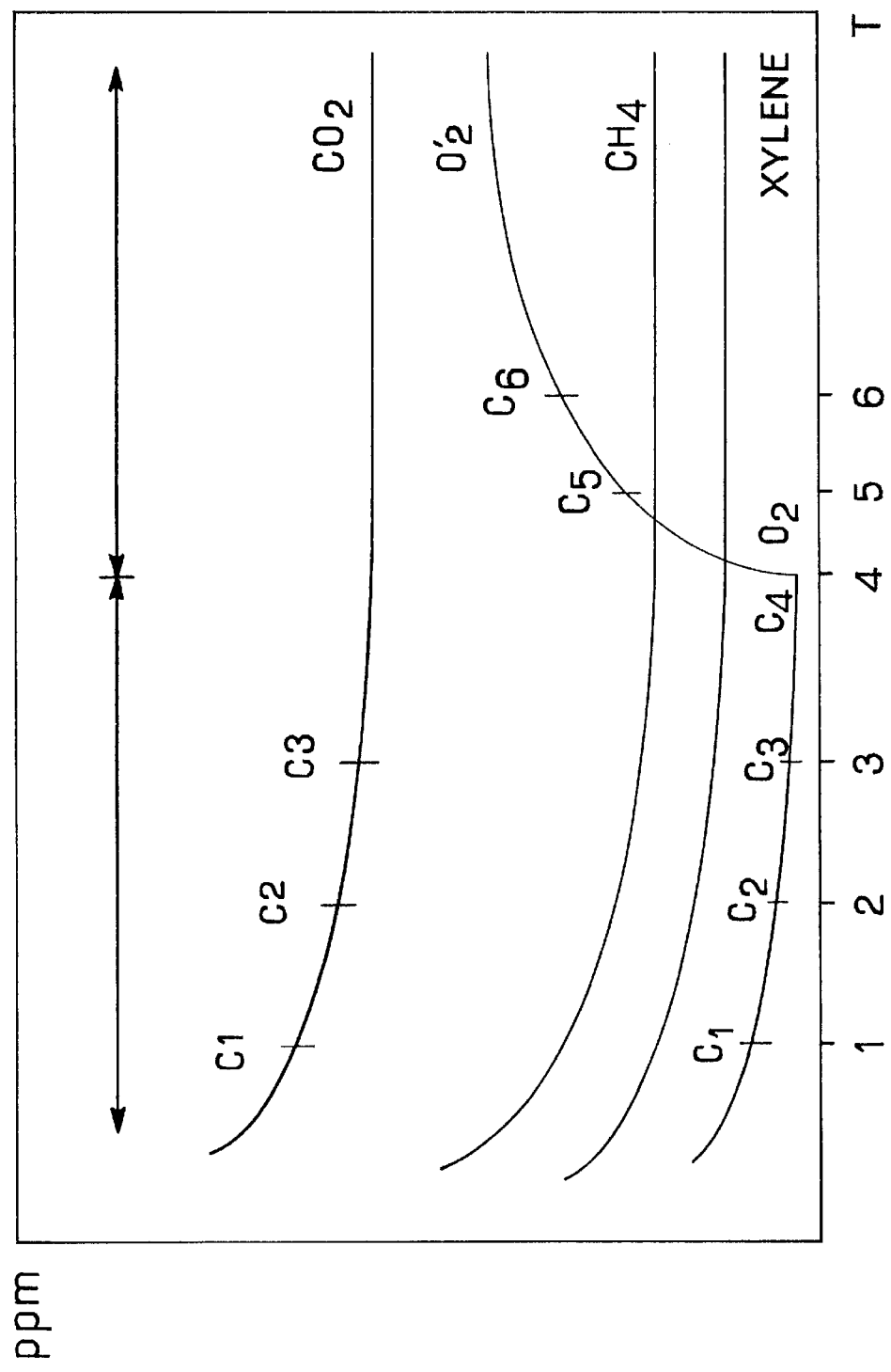
FIG. 3 is an experimental data graph of the concentrations of several gazeous elements as a function of time, as could be measured from fluid samples collected from a contaminated soil.

FIGS. 1 and 2 show a probe 10 according to the invention which is to be driven through and inserted into a body of earth 5 located beneath ground level. Contamination by one or more contaminant fluids is to be tested into earth 5. Probe 10 is the same as the one disclosed in our co-pending U.S. patent application No. 08/718,505, now U.S. Pat. No. 5,786,527, and comprises an outer cylindrical conduit 12 having an interior axially extending passageway 14. Located near the lower portion of conduit 12, there are provided a plurality of radially extending passageways 16 which are in fluid communication with axial passageway 14.

Located at the lower extremity of conduit 12 is a probe tip assembly 18, which includes a lower portion having tapered side walls 20 and 22 to form a boring tip 24 for soil penetration.

Probe tip assembly 18 also includes an upper cylindrical portion 26 which has exterior screw threads 28 thereon. Cylindrical portion 26 also includes an interior axial passageway 30 and a plurality of radially extending passageways 32 which are in fluid communication with axial passageway 30.

Cylindrical portion 26 engages with its threads an adaptor 34 which in turn engages with threads the lower end of conduit 12. In this respect, adaptor 34 is screw threadedly engaged in a conventional manner with conduit 12, while probe tip 18 is reverse screw threadedly engaged with adaptor 34.

At the upper end of conduit 12, there is provided a T adaptor generally designated by reference numeral 42. T adaptor 42 includes an outer housing 44 and has an axially extending passageway 46 extending therethrough with a transverse passageway 48 being in fluid communication therewith. T adaptor 42 is screw threadedly engaged with conduit 12 and there are provided conventional connecting fittings which are designated by reference numeral 50. Extending through axial passageway 46 of T adaptor 42 and through axial passageway 14 of conduit 12 is an interior conduit 52 which has an interior passageway 54 therein. Interior conduit 52 is connected to probe tip 18 such that continuous fluid communication is provided between passageway 30 of cylindrical portion 26 and passageway 54 of inner conduit 52.

In use, probe 10 is driven transversely through ground level and into soil 5 which is to be tested. During insertion, probe tip 18 is fully screw threadedly engaged with adaptor 34, i.e. all of cylindrical portion 26 is within adaptor 34, and thus radial passageways 32 are also covered by adaptor 34. This prevents earth from getting stuck in and obstructing passageways 32.

Once probe 10 is inserted to the desired depth, rotation of conduit 12 will cause probe tip 18 to partly disengage adaptor 34 and to assume its extended position as shown in FIG. 2—probe tip 18, being frictionally stuck in the soil 5, will tend not to rotate. This will thus allow fluid communication between the surrouding soil formation and passageways 32.

With this arrangement, a purge gas can be injected through conduit 14 and out of radial passageways 16, while collection of the gazeous contaminants is achieved by intake of fluid samples through radial passageways 32 wherein the fluid will flow through passageway 30 and passageway 54 of conduit 52 to a suitable testing apparatus (not shown).

Thus, probe 10 is generally used to test soil contamination by at least a first fluid, and allows fluid inlet and outlet to be accomplished through separate inner passageways or conduits.

The method of soil contamination testing according to the present invention will now be described.

The method is used for locally testing soil contamination preferably for toxic fluids, by determining the generation rate of a first contaminant fluid in porous soil. The contaminant fluid can be, for example, methane, xylene, carbon dioxyde, or any other suitable toxic or non-toxic fluid.

The probe 10 is inserted into the soil where testing is to be accomplished, at a selected depth. Then, a second fluid is injected in a continuous and constant flow through the probe radial passageways 16 into the soil. The second fluid is preferably an inert gas, for example helium or argon, or a substantially inert gas such as nitrogen. An inert gas is particularly desirable since it is not likely to become part of a chemical reaction with the contaminant fluid.

While the second fluid is injected into the soil, fluid samples are collected through the probe tip 18 through radial passageways 32 at regular time intervals, preferably at least at every minute. Although the gas collection is accomplished at least at regular time intervals, a continuous gas collecting is within the scope of the present invention. The concentrations of the first contaminant fluid can be measured from the collected sample, and this is accomplished until the variation of the first fluid concentrations in successive fluid samples becomes substantially equal to zero, i.e. a substantial equilibrium is achieved between the first and second fluid such that the first fluid concentration remains substantially constant over time. This step is carried out for a period of time sufficient to desirably achieve a relatively constant measurement of the contaminant. This period of time will usually extend from between one to ten minutes, although it will be understood that the time may vary depending upon the particular contaminant being tested and other parameters.

In certain instances, and due to the capacity of some portable test equipment, the concentrations of the volatile or gazeous contaminant may be used as representative and usable results without waiting for relative stabilization of the said concentrations. Indeed, it is possible to mathematically correlate the concentration equilibrium value of the first fluid from the concentration values and the rates of change thereof. It will be supposed, however, that the equilibrium of the first fluid concentrations are effectively reached.

Once the equilibrium is reached, a small quantity—relative to the second fluid—of a tracer gas is injected into the soil through probe tip radial passageways 16 simultaneously with the second fluid and at a constant flow rate. The tracer gas can be for example oxygen, helium, argon or hexafluoride; in any event the tracer gas should be of a different chemical structure than the second fluid, and of low concentration in the total second fluid and tracer gas mix, e.g. 0,25% of the total composition. The fluid sample collecting is continued in continuous real time or at regular time intervals for measuring the concentrations of the first contaminant fluid therein, and most importantly the concentrations of the tracer gas are also measured from these fluid samples.

The chemical equilibrium state achieved in the soil between the first contaminant fluid and the second fluid and tracer gas, is enabled by the fact that the soil has porosity; since most soils are porous, this is not very limitative. Thus, the injected second fluid and tracer gas will effectively cause the immediate surrounding soil volume to become a medium in which fluid equilibrium will eventually be reached with the first contaminant fluid.

With the measured concentrations of the first fluid and tracer gas, the generation rate of the first fluid can then be computed. The concentrations of the second fluid need not be measured, as its only purpose is to allow the first fluid to come into a state of equilibrium therewith. The invention, as previously discussed, is very suitable for measuring the presence of a volatile or a gazeous contaminant. However, it will be understood that the method could also be used with other fluids, including liquids.

The method described hereinabove will be more readily understood in view of the following experimental example.

Soil contamination by carbon dioxide, methane and xylene is to be tested. A probe as described hereinabove is inserted into the ground at a selected depth, e.g. down to two meters. Nitrogen is then injected continuously into the porous soil at a constant flow rate of approximately 1,5 liters/minute (li/min) to 2 li/min. At each one minute interval, fluid samples are collected from the soil by the probe, and the carbon dioxide, methane, xylene and molecular oxygen ($O_2$) concentrations are measured in the collected fluid samples. A chemical equilibrium state is known to be established between the above-mentioned contaminant chemical elements and the injected nitrogen when the variation of the concentrations of the above-mentioned measured contaminants becomes substantially equal to zero. That is to say, from that point on in time, the gaseous emmanations from the four above-mentioned measured elements from the soil into the nitrogen environment are substantially equal to the soil purge of said measured elements in addition to the probe collection of these elements.

At this point, e.g. after a few minutes of nitrogen injection (e.g. four minutes), a relatively small trace amount of oxygen, e.g. 5 ml/min, is injected into the soil in addition to the nitrogen. This small amount of oxygen added to the nitrogen should not be sufficient to upset chemical equilibrium state obtained in the soil. Fluid samples continue to be collected at each one minute interval, with corresponding measurements of the four above-mentioned elements.

The graph of FIG. 3 schematically shows results of the concentration measurements from the collected fluid samples. In this case, oxygen was already present in the soil, but this will not hinder the method since the oxygen generation rate in the soil is very small. If the measured concentrations of oxygen seem to yield that it is significantly present or that the soil generation rate of the oxygen is relatively high, enough to hinder the present method, then a different tracer gas should be used, such as hexafluoride.

It can be seen in the graph of FIG. 3 that the oxygen injection resulted in a noticeable increase of the oxygen concentration in the collected fluid samples starting at the four minutes mark, i.e. at the moment the oxygen started to be injected.

Equation (1) allows a H constant during the oxygen injection to be computed. The H constant can be obtained mathematically, and allows the soil generation rate of one or more fluid contaminants to be computed when the concentrations of the tracer gas are also computed. Equation (1) reads as follows:

$$H_{O2}=(C_6-C_5)/(C_5-C_4) \quad (1)$$

where $C_i$ (with i=1, 2, 3, . . . ) is the concentration of the measured chemical element, in this case $O_2$, at a given time i, in minutes. Thus, the H constant during oxygen injection is to be used with $i \geq 4$, since in this example the oxygen injection started at the four minute mark.

The maximum concentration of $O_2$, $C_{max}$, may then be computed, with equation (2):

$$C_{max}=(C_5-C_4*H_{O2})/(1-H_{O2}) \quad (2)$$

With this, the effective flowrate, Q', in the affected area surrounding the probe tip, called the affected soil volume, can be computed with equation (3):

$$G_{O2}/C_{max}=Q' \quad (3)$$

where $G_{O2}$ is the generation rate of oxygen in the soil, which is a known value, since it is injected by the operator through the probe (the effective generation rate of oxygen by the soil is not significant, as discussed hereinabove). Thus, the value of the effective flow rate into the affected soil volume becomes known.

The portion of the graph wherein nitrogen injection only is accomplished—i.e. from 0 to 4 minutes—is then used to determine the soil generation rate of each of the three other contaminant components (the oxygen generation rate can also be computed in the same manner). For each component, the constant H must first be calculated with equation (4):

$$H=(C_3-C_2)/(C_2-C_1) \quad (4)$$

Afterwards, the minimum concentration of a particular component is established with equation (5):

$$C_{min}=(C_2-C_1*H)/(1-H) \quad (5)$$

where H has been found in equation (4). Finally, equation (6) yields the generation rate, G, of the computed element:

$$G=Q'*C_{min} \quad (6)$$

where Q' has been computed from equation (3) and $C_{min}$ from equation (5).

The generation rate retrieved from equation (6) will be a volume per time unit, e.g. in liters/minute, or a mass per time unit, e.g. in milligrams/minute.

As can be seen graphically in FIG. 3, the measured concentrations of the different elements which are present in the collected fluid samples that are used to compute the soil generation rate of these elements, are the concentrations measured in the first portion of the graph, during the injection of the nitrogen.

A method as described hereinabove yields results that will not only give a measure of the contaminant concentrations in the soil where the testing has occured, as with many known methods, but also will allow to determine the local soil generation rate of contaminants. The latter will allow for example to determine whether recent or old contamination has occured where testing is accomplished. Indeed, to old contamination will correspond a very small or absent generation rate, whereas a recent contamination will correspond to a higher generation rate. This is particularly advantageous relative to the prior art methods, including the Wise method discussed in the Background of the Invention section of the present specification.

It is understood that any modifications which do not deviate from the scope of the present invention, are considered to be included therein.

For example, it is within the scope of the present invention that the tracer gas be injected at the beginning of the process, whereby the tracer gas and the second fluid (inert gas) are injected simultaneously upon initiation of the process. This would have to be accomplished with a tracer gas which is not intrinsically present in the soil, e.g. with hexafluoride, since using a tracer gas such as oxygen which can be present in the soil would be likely to yield erroneous results if the oxygen injection was started before the equilibrium is reached. If the tracer gas is injected at the beginning of the process, instead of waiting for the equilibrium, then all the measurements may be accomplished before the equilibrium is reached.

However, using another tracer gas than oxygen is not the preferred way to carry out the present invention, due to the more expensive equipment required to measure these other tracer gases, and also since it is more expensive to obtain another tracer gas than simply using the surrounding air to obtain the desired oxygen concentration.

I claim:

1. A method for locally testing underground soil contamination by determining the generation rate of a first contaminant fluid in porous soil, said method comprising the steps of:
    a) continuously injecting a second fluid in the soil at a substantially constant flow rate;
    b) simultaneously collecting fluid samples in the soil at least at regular time intervals near the area where said second fluid is injected in the soil;
    c) measuring the concentrations of said first fluid in the fluid samples collected in step b);
    d) once there is substantially no variation of the concentration of said first fluid in successive fluid samples according to the measurements accomplished in step c), injecting—in addition to said second fluid—a tracer gas at a constant flow rate and in a small quantity, relative to said second fluid;
    e) at the latest once step d) is started, measuring the concentrations of said tracer gas in the fluid samples collected in step b); and
    f) computing from the concentrations measured in steps c) and e) the first fluid generation rate in the soil.

2. A method as defined in claim 1, further comprising before step a) the step of inserting into and through the soil an elongated hollow probe having a lower end with inlet and outlet openings respectively connected to inlet and outlet conduits; whereby the fluid injection in steps a) and d) is accomplished through said outlet conduit in said hollow probe, and the fluid collection in step b) is accomplished through said inlet conduit in said hollow probe.

3. A method as defined in claim 1, wherein said second fluid is a substantially inert gas.

4. A method as defined in claim 3, wherein said second fluid is a gazeous fluid selected from the group comprising helium, argon and nitrogen.

5. A method as defined in claim 1, wherein said tracer gas is selected from the group comprising oxygen, helium, argon and hexafluoride; and said tracer gas is of different chemical structure than said second fluid.

6. A method as defined in claim 1, wherein fluid samples are collected for at least several minutes at one minute time intervals in steps b).

7. A method as defined in claim 1, wherein fluid samples are collected in step b) for at least several minutes in a continuous fashion.

8. A method as defined in claim 1, wherein the flow rate of the tracer gas being injected is approximately 0,25% of the flow rate of the second fluid being injected.

9. A method for locally testing underground soil contamination by determining the generation rate of a first contaminant fluid in porous soil, said method comprising the steps of:
    a) continuously injecting a second fluid and a tracer gas in the soil at substantially constant respective flow rates;
    b) simultaneously collecting fluid samples in the soil at least at regular time intervals near the area where said second fluid is injected in the soil;
    c) measuring the concentrations of said first fluid and of said tracer gas in the fluid samples collected in step b);
    d) computing from the concentrations measured in steps c) the first fluid generation rate in the soil.

10. A method as defined in claim 9, wherein fluid samples are collected in step b) for at least several minutes in a continuous fashion.

* * * * *